United States Patent [19]

Brugnoli

[11] Patent Number: 4,658,832

[45] Date of Patent: Apr. 21, 1987

[54] PORTABLE DEVICE FOR THE SURVEY OF THE BREATHING VENTILATION AND OF THE OXYGEN CONSUMPTION, CONNECTED BY MEANS OF RADIO SIGNALS TO A FIXED RECEPTION AND ELABORATION STATION

[75] Inventor: Siro Brugnoli, Rome, Italy

[73] Assignee: COSMED S.r.l., Rome, Italy

[21] Appl. No.: 733,543

[22] Filed: May 13, 1985

[30] Foreign Application Priority Data

Apr. 1, 1985 [EP] European Pat. Off. ........ 85830081.7

[51] Int. Cl.⁴ .............................................. A61B 5/08
[52] U.S. Cl. .................................. 128/719; 128/726; 73/861.77
[58] Field of Search ............... 128/716, 719, 720, 725, 128/726, 727; 73/861.77

[56] References Cited

U.S. PATENT DOCUMENTS

| | | | |
|---|---|---|---|
| 3,605,729 | 9/1971 | Liu et al. .............................. | 128/726 |
| 3,645,133 | 2/1972 | Simeth et al. .................... | 128/725 X |
| 3,896,792 | 7/1975 | Vail et al. ......................... | 128/725 X |
| 3,922,525 | 11/1975 | Kozak et al. .................... | 128/725 X |
| 4,078,554 | 3/1978 | Le Maitre et al. ................... | 128/726 |
| 4,140,106 | 2/1979 | Kirmaier .......................... | 128/726 X |
| 4,282,883 | 8/1981 | Yerushalmy ....................... | 128/726 |
| 4,368,740 | 1/1983 | Binder .............................. | 128/725 X |

FOREIGN PATENT DOCUMENTS 627359  1/1982  Switzerland ........................ 128/726
856621  12/1974  U.S.S.R. ............................... 128/726

Primary Examiner—Carlton R. Croyle
Assistant Examiner—Paul F. Neils
Attorney, Agent, or Firm—Beveridge, DeGrandi & Weilacher

[57] ABSTRACT

A device for the survey of the breathing ventilation and oxygen consumption has a mask M, worn by the person being examined, a control modulus that realizes a sample method of the breathing volume and of the turnover management, and a radio transmitter 25 that sends the signals to a fixed reception and elaboration unity UF. The device is portable due to the very small dimensions thereof, and very light due to the presence of a slow analyzer that has the advantages of the quick analyzers, by means of controlled turnover sampling that makes the micro mixing chamber 3 at fixed capacity equivalent to a dynamic chamber at variable capacity. At the end of each breathing action, when the air flow is annulled, the impulses due to the moment of inertia of the turbine 7 are suppressed by means of the pressure transducer 9 that identifies the annulment of the flow and corrects the signal still provided by turbine 7.

9 Claims, 4 Drawing Figures

PORTABLE DEVICE FOR THE SURVEY OF THE BREATHING VENTILATION AND OF THE OXYGEN CONSUMPTION, CONNECTED BY MEANS OF RADIO SIGNALS TO A FIXED RECEPTION AND ELABORATION STATION

The present invention concerns a device for the survey of the breathing ventilation and of the oxygen consumption connected by means of radio signals to a reception and elaboration station comprising a volume meter, an oxygen concentration meter, a control and a radio transmitter modulus of small dimensions and weight so as to be directly connected to the person being examined.

The meters known in the art do not allow a survey in the "real" conditions, i.e. during work or sport, and therefore static laboratory analysis must be peformed.

In these situations it is impossible to obtain such conditions that are however necessary for a valuation of the breathing functionality in "limit" conditions—like the ones of an athlete in a contest or during training, or of a person working in conditions that could prove to be dangerous for his health (smoke, smog, noise, heat, etc.).

It is known that breathing ventilation (VE) means the air volume expired by a person in one minute; while oxygen consumption VO2 means the volume of oxygen consumed in one minute while breathing.

The VO2 is given by the product of the ventilation per minute multiplied by the difference between the inhaling and expiration oxygen concentration.

The average expiratory concentration must be calculated because during expiration, the oxygen percentage is not constant.

The VO2 calculation is completed with the survey of ambient pressure, temperature and moisture values that allow to bring back the measure of VO2 to "standard" conditions provided for the gaseous volumes (20° C., 760 mmHg, 0% relative moisture).

The volume meters actually known are of the kind:
(1) closed circuit
(2) open circuit.

Between the closed circuit volume meters the type most used are:

(a) container or piston.

In this case, a cylinder is moving inside another one in function of the gas that is let in and out. The sealing between the two cylinders is obtained by membranes or immersing the movable cylinder in a liquid contained in the second cylinder.

(b) Bellows.

The volume is obtained by the capacity variation of the bellow. The most used are the angular variation bellows like the ones used to blow on a fire.

The volume meters with open circuit actually most used are:

(a) a pneumotacograph of Fleisch and Lilly.
Both are based on the principle of the Venturi tube.
(b) Hot wire.

This has an element whose electric features (e.g. the resistance) vary according to the speed of the air flow that strikes it.

(c) Turbine or fly.

This performs a number of revolutions proportional to the volume that strikes it.

The turbine device already known is disadvantaged due to the inertia moment due to the rotation of the propeller around the axis.

Infact, the turbine continues to rotate, even when the flow striking the same is annulled, for a time period (the time of arrest) inversely proportional to the resistance and to friction within the system.

It is not possible to increase the friction beyond determined limits for reducing the time of arrest, because to each friction increase corresponds a minimum flow (threshold) increase, that places the turbine into rotation, and below which no good signal is obtained because the turbine remains still.

It is evident that the "ideal" turbine meter is the one having a threshold flow and a time of arrest being nul.

The most used devices for measuring oxygen concentration may be grouped in three main classes:
(1) thermoparamagnetic (or at magnetic wind);
(2) magnetodynamic (or pure magnetic);
(3) electrochemical, in turn divided into polarographic and galvanic.

A further classification of the analyzers may consist in using as a reference parameter the response time (tr) of the instrument:
(1) QUICK analyzers (tr<200 ms);
(2) SLOW analyzers.

The difference between the two classes is not limited to the response time as therefore this time has a considerable influence on the other technical features.

The stability and the exactness of a SLOW analyzer, are considerably better than those of a QUICK analyzer.

Usually, when high stability is required, it is necessary to keep the instrument continually working, around the clock, if it is a QUICK analyzer, while only a few minutes are sufficient for reaching the speed conditions if it is a SLOW analyzer.

This is due to the different chemical and physical features of oxygen, that are utilized in the two kinds of instruments to obtain the value of the concentration.

Furthermore, QUICK analyzers are extremely sensitive to pressure, temperature and moisture variations that take place inside the measuring chamber.

For example, in all known analyzers it is preferred that the gas flow to be measured be constant (0.5 or 1 l/min).

Otherwise there will be enormous measuring errors.

It can therefore also be easily understood that auxiliary devices, such as the aspiration pump, must have the features of exactness and stability.

The foregoing demonstrates the difference between the two kinds of analyzers in terms of cost and practicability in use.

Usually, a QUICK analyzer is five to ten times more expensive that a SLOW one. Furthermore, due to the particular functioning, mainly for what concerns stability, a QUICK analyzer is not suited for being carried about while it functions.

Also the fact that the QUICK analyzer is heavier and requires more space than a SLOW one, should be considered.

The only advantage of a QUICK analyzer is therefore, the fact that measurements can be taken in a real time.

In the medical use this means that it will be possible to "follow" phenomena that quickly vary during a determined period, without losing information.

For what concerns the methods actually used for the survey of the oxygen percentage there are, the same concerns:

(a) the momentary measuring of the oxygen percentage present in the expired gas and the following calculus of the average value; and (b) the direct measuring of the oxygen average expiratory percentage effected by means of a "mechanical mediator".

For momentary measuring QUICK analyzers are used the response time thereof not exceed 150/200 msec.

Gas sampling will be effected near the person's mouth.

On the contrary, the direct measuring of the average oxygen value may be effected with quick as well as with slow analyzers.

For obtaining the average value, the expired volume will be sent into a chamber, for the mixing of the expired gases, that works as "mechanical mediator".

When the measuring of the oxygen percentage inside the chamber is effected by means of a quick analyzer, the capacity of the same does not represent particular difficulties because the quickness of the analyzer assures a correct measure independently from the volume expired by the person.

If, on the contrary, a slow analyzer is used, the chamber's capacity will have to be determined according to the response time of the analyzer and of the ventilation.

Usually, oxygen consumption measuring is effected at regular time intervals (e.g. each 30 seconds). This means that between one measure and the other, a determined gas volume must be collected in the chamber, representative, in terms of an average oxygen percentage, of the time interval being examined.

Usually, "turnover" shows how many times in one minute a volume equal to the one of the chamber has passed inside the same so as to obtain the so-called "washing speed of the chamber".

To prevent the concentration measuring during one calculation interval from being influenced by the oxygen percentage values relating to the precedent interval, it is necessary to provide a minimum turnover number $T_{min}$ that assures the "renewal" of the mixing chamber.

On the other hand, the response time of the analyzer is such as to impose a limit also for the maximum turnover number $T_{max}$.

In other words, for a too low ventilation the renewal of the chamber is not quick enough. Therefore the oxygen percentage is influenced by the values of the foregoing interval.

The ventilation, being an independent variant, the only term on which it is possible to act is the capacity $C$ of the mixing chamber. The same must be such as to satisfy the relation:

$$T_{min} \times C < VE < T_{max} \times C.$$

Once the values of $T_{min}$ and $T_{max}$ are fixed at a determined capacity value of the chamber C, it can be seen that the ventilation may vary between a minimum $VE_{min}$ and a maximum $VE_{max}$.

It will be necessary to modify the value of C according to VE for removing this obstacle.

This infact is the main principle on which the so-called "dynamic" chambers at variable capacity are based.

The known devices use static as well as dynamic chambers.

Usually the capacity of the same varies between about two to twelve litres.

A further method for the measuring of the average expiratory concentration is known, and it consists in the continuous taking of a sample (e.g. 1/100) of expired gas to be sent into a micro mixing chamber. This allows considerable reduction of the capacity and therefore the dimensions of the chamber.

As during the exipiration phase the oxygen percentage is not constant, the sampling flow shall be proportional to the expiration one so that the sample taken from the mouth is representative of the expired volume.

This method may be compared to the one realized by means of a fixed mixing chamber to which all the expired volume is sent. It is evident that the same limits are considered for the fixed chamber, considering that between the two methods there is only a capacity difference of the chambers due to the sampling.

Usually the systems for measuring the VE and the VO2 are cumbersome and heavy devices, so that the use thereof must be limited to the laboratory.

For what concerns the so-called "portable" systems, there are instruments that weigh about 8 kg, resulting from the miniaturization of some fundamental elements; but the weight and dimension don't make them suitable for performing any sport activity therewith, except riding a horse or a bicycle.

Furthermore, the method for the calculation of the oxygen percentage is the one of the fixed mixing chamber. Therefore, this is a traditional system and the weight and dimensions thereof do not solve the problems of carrying it about during its use.

Said system is completed by a microcomputer and by a small tape recorder that allows a late data elaboration.

It is the aim of the present invention to reduce the dimensions and the weight of a device for the survey of breathing ventilation and oxygen consumption so as to directly connect it to the person to be examined during work or sport activity.

The aim set forth is reached by means of a device characterized in a portable survey and transmission unit connected, by means of radio signals, to a fixed reception and elaboration station.

The portable unit, carried by the person to be examined, comprises a breathing mask supporting the devices for the survey of the ventilation and temperature signals as well as for the expiratory volume sampling.

The signals are provided to a radio control and transmission modulus, these elements also being carried by the person by way of a belt on the person so as not to disturb his physical activity.

The control modulus activates the circuit that realizes the special method of sampling of the expiratory volume and of the turnover management, thus also obtaining the signal relative to the oxygen percentage.

The transmitter sends the signals to the fixed reception and elaboration station.

The present invention is explained more in detail hereinbelow according to the attached drawings in which a preferred embodiment is shown.

Figure 1:
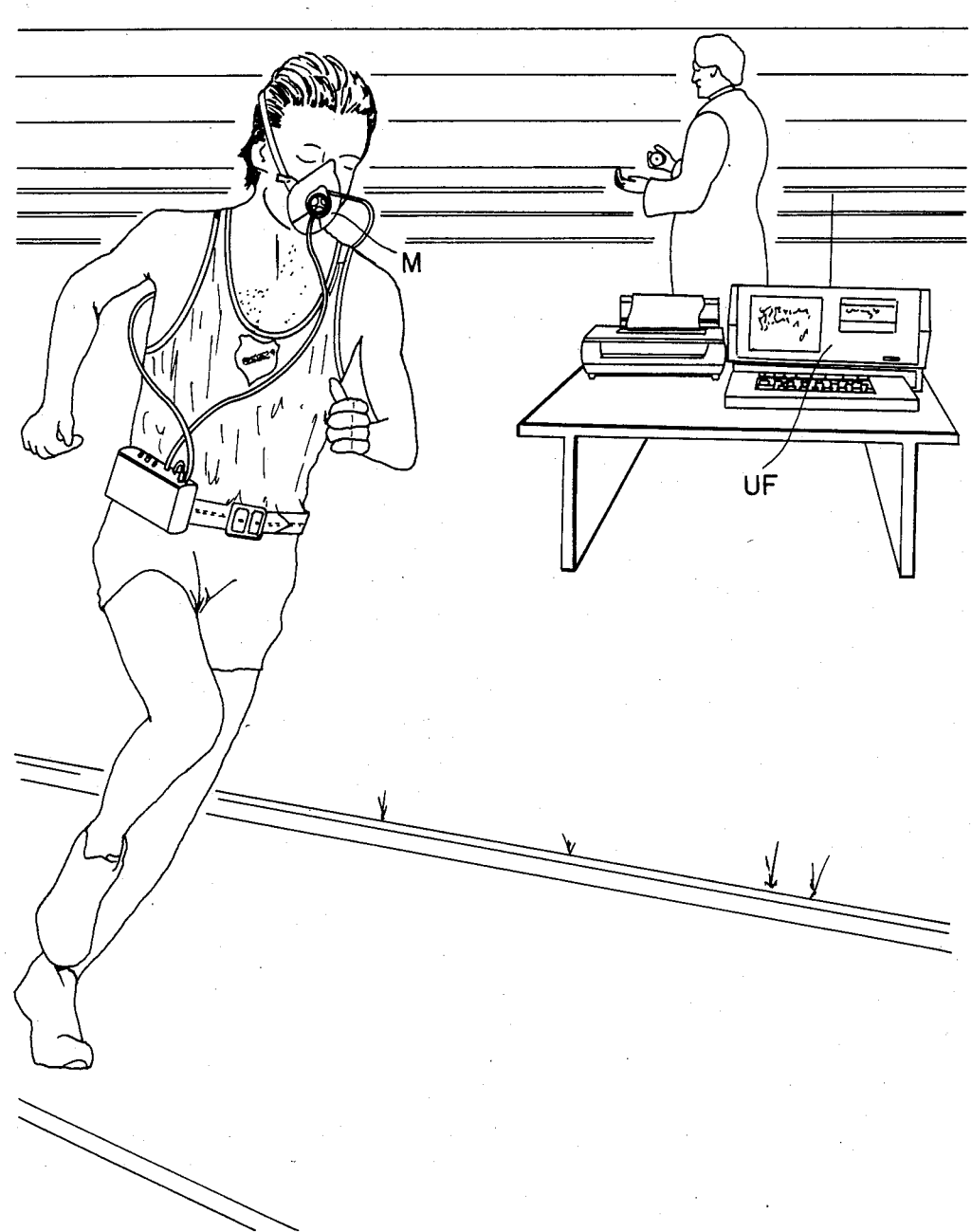
FIG. 1 is a perspective view of a device used by an athlete while running in accordance with the present invention.
Figure 2:
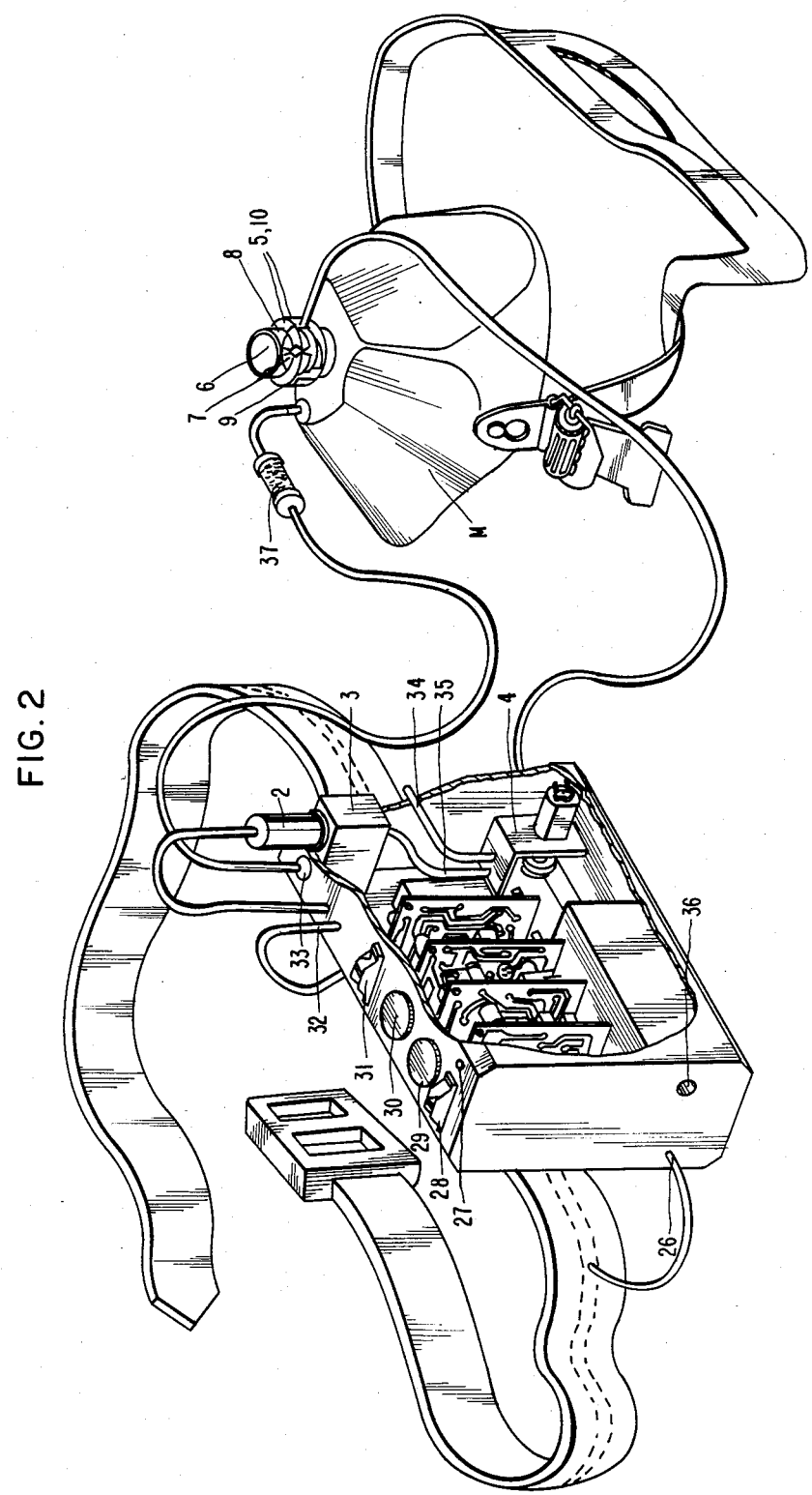
FIG. 2 shows a perspective and cross-sectional view of a device for the survey and transmission of data.

The figures show a portable device for the survey of the breathing ventilation and of the oxygen consumption connected by means of radio signals to the fixed reception and elaboration station UF, comprising an oxygen meter 2 with a polarographic electrode, a sampling pump 4, a photo diode sender 5, a volume survey system 6, a turbine 7, a temperature sensor 8, a pressure transducer 9, a photo surveyor 10, an oxygen annulment 20, an oxygen amplification adjuster 21, a radio transmission antenna 26, an accumulator charge level indicator led 27, a starting switch 28, an automatic gauge switch 31, a mask connection cable 32, an inlet 33 of the mixing chamber, an outlet 34 of the sampling pump, an outlet 35 of the mixing chamber, a connector 36 for accumulator charge, and a moisture absorber 37.

Figure 3:
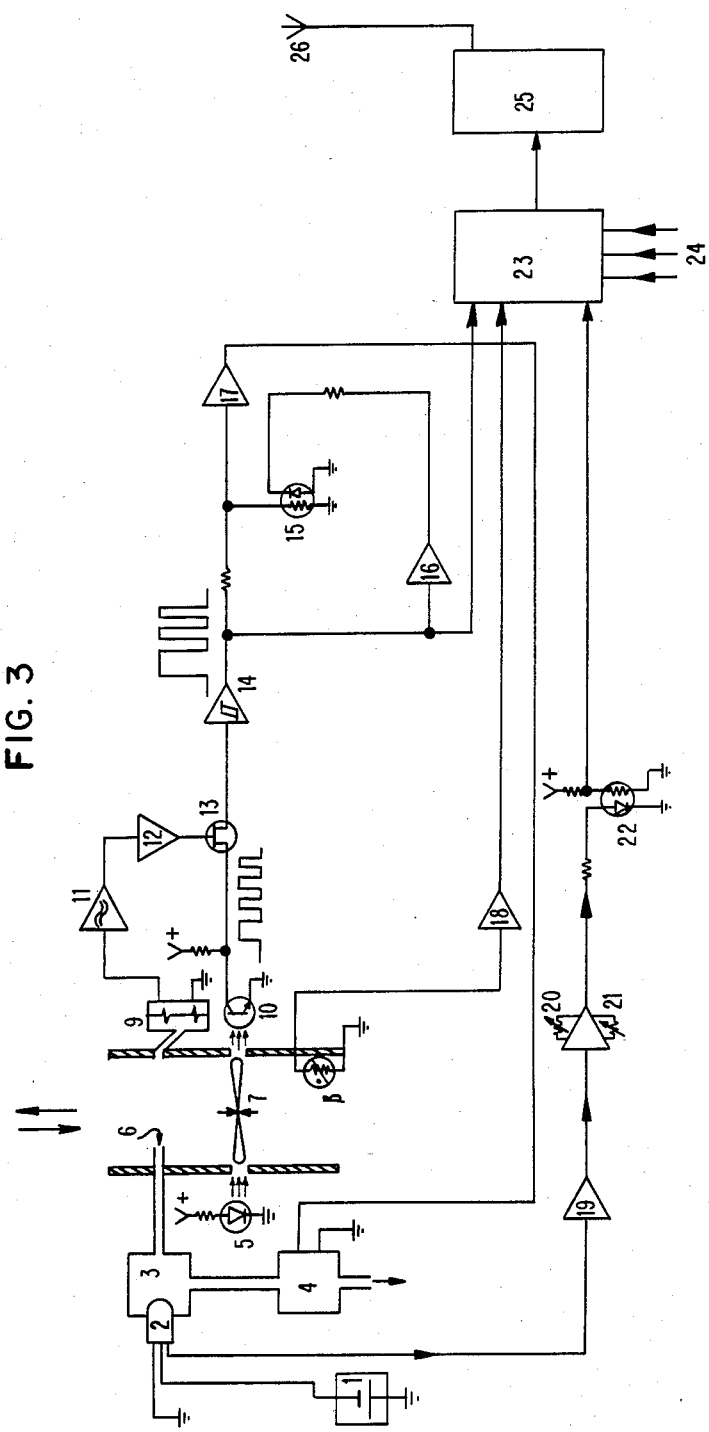
FIG. 3 shows in partial schematic form, a circuit suitable for incorporation into the device according to the present invention.

In FIG. 3, beyond the already mentioned details, there is shown: a circuit 1 an oxygen electrode polarizer, an electronic filter 11, a comparator 12, a transistor FET 13, a Schmitt TRIGGER 14, a photo resistor 15, an integrator 16, a power amplifier 17, a (temperature) amplifier 18, an (oxygen) amplifier 19, a photo resistor 22, a radio frequency modulator 23, auxiliary inlets 24 (ECG, SaO2, etc.), and a radio transmitter 25.

For what concerns the turnover management, the present invention acts on the value of $F=Fe/Fc$, where Fe is the expiratory flow and Fc is the sampling flow, instead of on $C=$ chamber capacity, thus obtaining a mechanical mediator; the functioning thereof may overlap—for what concerns the result—the one that could be obtained varying the capacity of a dynamic chamber being F times bigger.

The measuring of the ventilation will be effected, according to the present invention, by means of a high precision traditional turbine 7 and a pressure transducer 9, that are suited for a practical and economical recognition of the nul flow that eliminates the problems due to the "arrest time" of the turbine.

Inside the tube containing turbine 7, a pressure transducer 9 (e.g. a microphone) will be inserted, for recognizing in a nul time the flow conditions different from zero.

Transducer 9 provides an output signal proportional to the pressure and therefore to the air flow striking the same with a response time of less than 1 msec.

In other words, the transducer may be used as an ON-OFF indicator for recognizing the flow annulment and thus correcting the signal the turbine continues sending during the arrest time.

Thus the main error source will be eliminated.

For what concerns the functioning of the device according to the present invention, the person is connected, by means of the mask M, to a gaseous volume survey system 6, including turbine 7 rotating at a speed proportional to the air volume striking the same.

The photo diode system 5 and the photo surveyor 10 generate an impulse train proportional to the number of revolutions of the turbine.

As already shown, at the end of each expiration and inhaling, when the air flow is annulled, the impulses obtained due to the inertia moment of turbine 7 are suppressed by means of a correction circuit including pressure transducer 9 that immediately reveals (less than 1 msec) the flow annulment.

The output signal of tansducer 9, filtered by circuit 11, is sent to comparator 12 that controls transistor FET 13, the ON-OFF functioning thereof allowing or preventing the transmission of the impulse train to an amplifier, Schmnitt trigger circuit 14.

The filter 11 also allows the elimination of the impulses generated during the inhaling stage.

The impulse train present at the Schmnitt trigger 14 output therefore represents "the correct expiratory volume" that is provided to modulator 23 to which the radio transmitter 25 is connected.

The same signal will be sent to a powder amplifier 17 that controls the capacity of the sampling pump 4 and to an integrator 16.

Integrator 16, by means of the photoresistor 15, controls the level of the inlet signal of the power amplifier 17.

The sampling flow of pump 4 is always proportional to the expiratory flow according to an amplification factor controlled by integrator 16, which therefore has the function of "automatic gain control".

The sample volume of pump 4 shall be sent to a micro mixing chamber 3 inside of which there is a polarographic electrode 2 for the measuring of the oxygen percentage.

The suitably amplified outlet of electrode 2 is connected to modulator 23 and to transmitter 25.

The system is completed with a sensor 8 for the survey of the expired gas temperature, the output thereof being amplified at amplifier 18 and sent to modulator 23 and transmitter 25.

The present invention also has connectors 24 for connection to receive auxiliary signals coming from other instruments, like ECG signals (electrocardiographic signal) or SaO2 signals (signal for the oxygen blood saturation.

Figure 4:
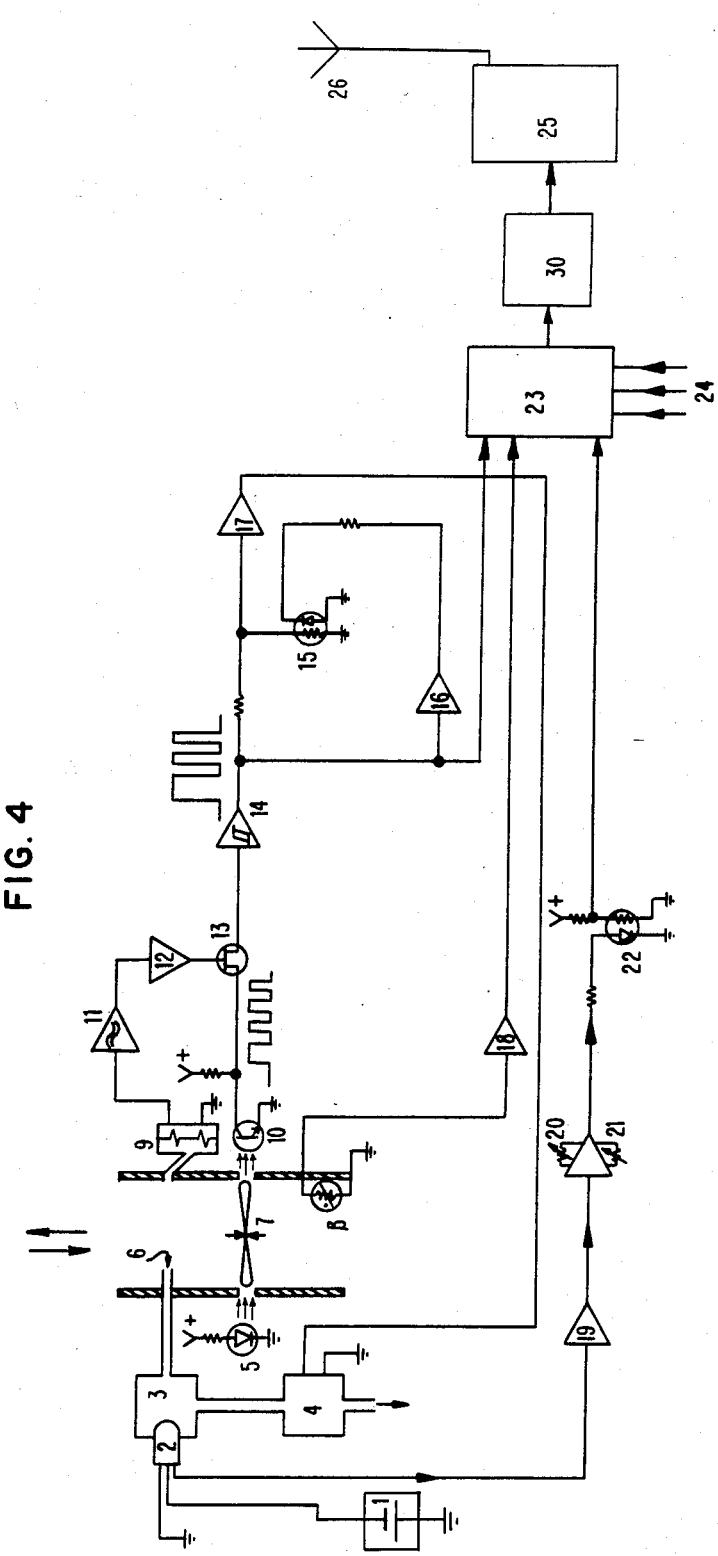
FIG. 4 shows in partial schematic form, another circuit similar to that of FIG. 3, also including a recorder.

FIG. 4 shows an alternative embodiment of the present invention that includes in addition to transmitter 25, a recorder 30, that will allow the late data analysis. Recorder 30 may be of the digital type, with an electronic memory. Alternatively, recorder 30 can simply comprise a tape recorder.

The main advantages of the present invention are the following:

(1) the presence, in the device, of a slow oxygen analyzer that guarantees, with respect to a quick one, a greater exactness and stability in measuring, beyond a smaller "criticity", at a cost five to ten times lower;

(2) the concept of sampling by means of a pump with variable capacity according to the expiratory flow allows to analyze, beyond the average value of the oxygen percentage, also the one relative to a "portion" of expiration. For analyzing "End breathing" values, i.e. those oxygen percentage values at the end of each expiration that are very important in the analysis of the breathing functionality, it will be enough to operate the sampling pump during the end of expiration, which can be easily recognized by the signal coming from the volume meter. Until now an analysis of this kind has been possible only by means of very expensive quick analyzers.

(3) The possibility of using a slow analyzer without renouncing to the advantages offered by the quick ones has allowed a great miniaturizing, that can not be obtained by any quick analyzer in commerce.

(4) The controlled turnover sampling makes the fix capacity micro mixing chamber equivalent to a dynamic chamber at variable capacity, with the advantage of a considerable dimension reduction.

(5) The controlled turnover annuls the limitation already listed for the slow analyzers, i.e. the incapability of these of covering the whole ventilation variation range.

I claim:

1. A portable device for surveying breathing ventilation and oxygen consumption, said device communicating by radio signals to a fixed reception and elaboration station, said device comprising a volume meter, an oxygen concentration meter, control and radio transmission means including a modulator connected to a radio transmitter, said radio transmission means being of small dimension and light weight so as to be carried by the person to be examined, said device comprising a gaseous volume survey system connected to a mask and including a turbine rotatable at a speed proportional to the speed of a volume of air striking the turbine, a photodiode system and a photosurveyor for generating pulses indicating the speed of rotation of the turbine, a pressure transducer for surveying air flow annulment, said transducer detecting the presence or absence of air flow through the turbine and providing an output signal on the cessation of air flow to prevent said photodiode system and photosurveyor from transmitting said pulses to a Schmitt trigger connected to said modulator and said radio transmitter, said Schmitt trigger being responsive to said pulses from said photodiode system and said photosurveyor to simultaneously provide an output signal to said modulator and said radio transmitter and to a power amplifier connected to said Schmitt trigger, said device further comprising an integrator for controlling the amplification factor of said power amplifier, a sampling pump, a micro-mixing chamber communicating with said pump, the gas flow through said pump being proportional to the expiratory flow and the capacity thereof being controlled by said power amplifier, and a polarographic electrode for measuring oxygen percentage, said electrode being connected to said modulator and said transmitter and providing an output signal thereto.

2. A portable device for surveying ventilation according to claim 1, further comprising a temperature sensor for sensing the temperature of the expired gases and providing an output signal indicative thereof, and an amplifier connecting said temperature sensor to said radio frequency modulator and said transmitter.

3. A portable device for surveying ventilation according to claim 1, further comprising an electronic filter, a transistor and a comparator connecting said filter to said transistor, said filter filtering the output from said transducer, said comparator controlling said transistor to act as a switch whereby in one state said transistor transmits said pulses from said photodiode system and said photosurveyor to said Schmitt trigger and in its other state, precludes transmission of said pulses.

4. A portable devide for surveying ventilation according to claim 1, wherein said device samples so as to reproduce inside the mixing chamber the same conditions as exist within a dynamic chamber, thus reducing the dimension and weight of said device, said device varying the drawing dynamic according to ventilation so that the response time of said polarographic electrode and of said mixing chamber is constant and the measuring of the concentration is not dependent upon the value of the breathing ventilation.

5. A portable device for surveying ventilation according to claim 1, further comprising auxiliary inlets for receiving auxiliary signals from other instruments such as an ECG and/or an SaO2, said device transmitting said auxiliary signals.

6. A portable device for surveying ventilation according to claim 1, further comprising a recorder.

7. A portable device for surveying breathing ventilation and oxygen consumption, said device comprising a volume meter, an oxygen concentration meter, and recording means for recording said survey, said device being light weight so as to be carried by the person to be examined, said device further comprising a gaseous volume survey system connected to a mask and including a turbine rotatable at a speed proportional to the speed of a volume of air striking the turbine, a photodiode system and a photosurveyor for generating pulses indicating the speed of rotation of the turbine, a pressure transducer detecting the presence or absence of air flow through the turbine and providing an output signal upon the cessation of air flow to prevent said photodiode system and photosurveyor from transmitting said pulses to a Schmitt trigger connected to said recording means, said Schmitt trigger being responsive to said pulses from said photodiode system and said photosurveyor to simultaneously provide an output signal to said recording means and to a power amplifier connected to said Schmitt trigger, said device further comprising an integrator for controlling the amplification factor of said power amplifier, a sampling pump, a micro-mixing chamber communicating with said pump, the gas flow through said pump being proportional to the expiratory flow and the capacity thereof being controlled by said power amplifier, and a polarographic electrode for measuring oxygen percentage, said electrode being connected to said recording means and providing an output signal thereto.

8. A portable device for surveying ventilation according to claim 7 wherein said recording means comprises a tape recorder.

9. A portable device for surveying ventilation according to claim 7 wherein said recording means comprises a digital recorder.

* * * * *